(12) United States Patent
Galick et al.

(10) Patent No.: US 7,078,539 B2
(45) Date of Patent: Jul. 18, 2006

(54) CARBONATE DECOLORIZATION

(75) Inventors: Paul E. Galick, West Chester, PA (US); Jude T. Ruszkay, Coatesville, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 477 days.

(21) Appl. No.: 10/611,831

(22) Filed: Jul. 1, 2003

(65) Prior Publication Data

US 2005/0004375 A1    Jan. 6, 2005

(51) Int. Cl.
*C07D 317/36* (2006.01)
*C07D 317/38* (2006.01)

(52) U.S. Cl. ...................... 549/230; 558/260

(58) Field of Classification Search ............... 549/230; 558/260

See application file for complete search history.

(56) References Cited

U.S. PATENT DOCUMENTS

| 4,204,956 A | 5/1980 | Flatow |
| 5,962,699 A | 10/1999 | Marquis |
| 6,042,698 A | 3/2000 | Beckett et al. |
| 6,384,240 B1 | 5/2002 | Machac et al. |

*Primary Examiner*—Kamal A. Saeed
*Assistant Examiner*—Michael P. Barker
(74) *Attorney, Agent, or Firm*—William C. Long

(57) ABSTRACT

The color of organic carbonate such as ethylene carbonate or propylene carbonate is substantially improved by ultraviolet irradiation.

4 Claims, 1 Drawing Sheet

CARBONATE DECOLORIZATION

BACKGROUND OF THE INVENTION

The present invention relates to a process for improving the color of organic carbonates such as alkylene carbonates by treatment with ultra violet radiation.

DESCRIPTION OF THE PRIOR ART

U.S. Pat. No. 5,962,699 provides a comprehensive description of the problems of discoloration of organic carbonates. The solution suggested in said patent involves a hydrogen peroxide treatment. Other methods for accomplishing the decolorization include distillation procedures as well as treatment with solid contact materials such as carbon, hydrotalcite and basic alumina. Reference is made to U.S. Pat. No. 6,384,240 as well as co-pending application Ser. No. 10/141,617 filed May 8, 2002. The disclosures of the above cited patents and application are incorporated herein by reference.

UV radiation has been used, for example, in water purification as shown in U.S. Pat. No. 4,204,956 and in isophorone color improvement as shown in U.S. Pat. No. 6,042,698.

BRIEF DESCRIPTION

Organic carbonates, especially alkylene carbonates such as ethylene carbonate and propylene carbonate are irradiated with ultra violet (UV) radiation for a time sufficient to significantly decolorize the carbonates.

DETAILED DESCRIPTION

Figure 1:
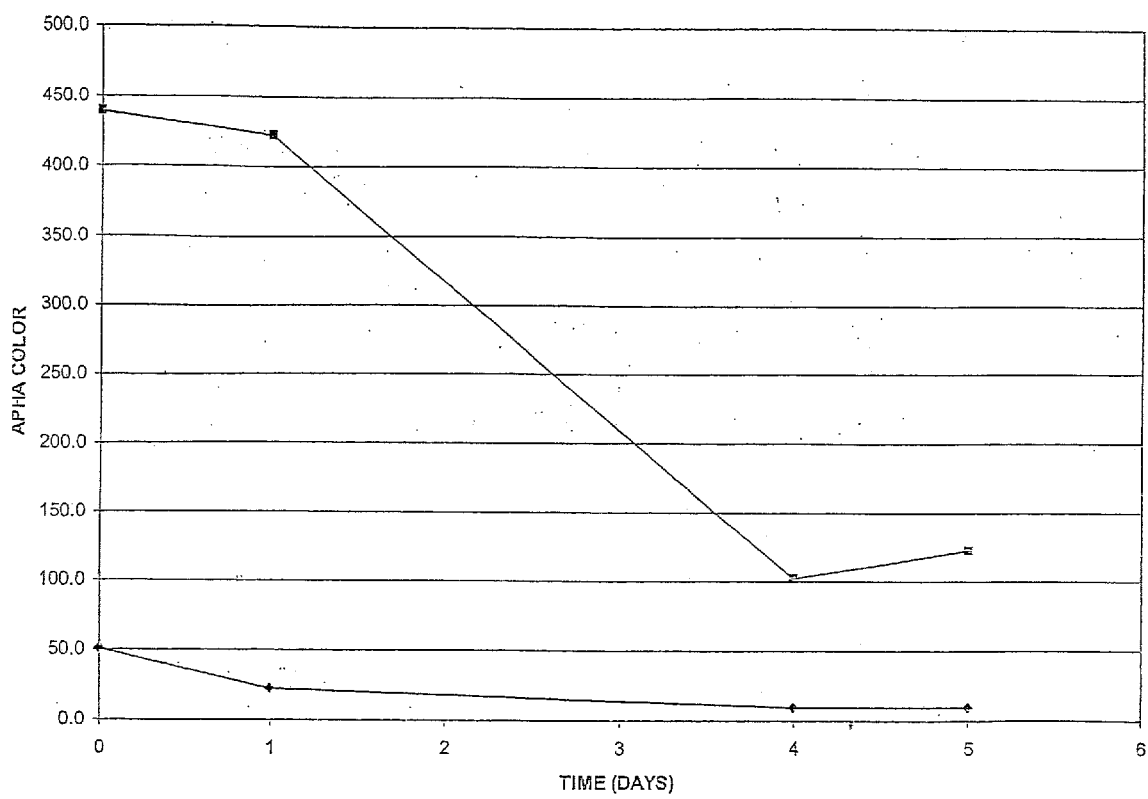
FIG. 1 is a graphical representation of the color improvement achieved as a function of time through practice of the invention.

For a description of the organic carbonates treated in accordance with the invention as well as the preparation thereof, reference is made to U.S. Pat. No. 5,962,699, the entire disclosure of which is incorporated herein by reference.

In practice of the instant invention, the color of an organic carbonate such as ethylene carbonate or propylene carbonate is improved by irradiation with UV light for a time effective to improve the color.

In practice of the invention, the organic carbonate for which color improvement is desired is irradiated with ultra violet light having a wavelength of 200–400 nanometers. Suitably, the light can be provided by fluorescent UV lamps which are commonly available. Both UV-A and UV-B lamps are suitable with the UV-B lamps which emit light in about the 280 to 315 nanometer wavelength range preferred. The rate at which color is improved is dependent on the rate at which ultra violet energy is provided. Generally, the higher the rate of energy provided the more rapid the color improvement.

In practicing the invention, illustratively a source of ultra violet radiation such as a UV-B lamp can be placed in a Quartz Tube, and immersed in liquid organic carbonate. Alternatively, the liquid carbonate can be caused to flow over a source of the ultraviolet radiation. Such procedures are generally quite well known in the field of water treatment and can be modified for use in the present invention. See, for example, U.S. Pat. Nos. 4,204,956 and 6,042,698 the disclosures of which are incorporated herein by reference.

The process can be carried out on a large scale by employing commercially available UV treatment cells (commonly used in water purification plants) and circulating the carbonate through the UV cells with a residence (irradiation) time sufficient to bring about the desired degree of color reduction. The wavelength of the UV radiation used is suitably in the region of about 200–400, preferably 280 to 315 nanometers as provided by conventional UV lamps.

The exposure of discolored carbonate to UV radiation may be carried out in several ways. The discolored carbonate may be exposed to the desired amount of UV radiation either in a single pass through the appropriate apparatus (the so-called "once through" system) or it may be exposed to the desired amount of radiation through multiple short passes through the appropriate apparatus (the so-called "batch circulation" system). Alternatively, a bath of discolored carbonate can be agitated within a vessel provided with a suitable source of UV light either at the top or on the side of such a vessel.

In order to achieve significant color improvement in accordance with the invention the alkylene oxide should be irradiated for a sufficient time, to achieve the improvement. Generally times ranging from 10 minutes to many days, eg. 10 or more days are useful.

It is noted that alkylene carbonates are routinely tested for UV absorbance. Such tests are on a small sample and are of short duration and do not produce the color improvement which is achieved through practice of the instant invention.

The invention can, perhaps, best be illustrated by the following examples.

Both a high purity propylene carbonate (99.6% pure) and a technical grade propylene carbonate (99.0% pure) prepared as described in copending application Ser. No. 10/141,617 filed May 8, 2002 were subjected to ultraviolet radiation using a UV-B QFS-40 fluorescent lamp over a five day period. The propylene carbonate samples were in glass tubes and temperature was about room temperature.

The experiment results are shown graphically in the attached FIG. 1 and are presented in the following Table 1.

TABLE 1

| Imadiation Time, days | APHA COLOR | |
|---|---|---|
| | High Purity PC* | Technical Grade PC* |
| 0 | 51.0 | 438.9 |
| 1 | 22.2 | 422.4 |
| 4 | 9.1 | 102.0 |
| 5 | 9.1 | 123.1 |

*propylene carbonate

It can be seen from these experimental results that the propylene carbonate color was substantially improved as a result of the ultra violet irradiation treatment of the invention.

We claim:

1. A method of improving the color of an organic carbonate which comprises irradiating the organic carbonate with ultraviolet light.

2. The method of claim 1 wherein the organic carbonate is ethylene carbonate.

3. The method of claim 1 wherein the organic carbonate is propylene carbonate.

4. The method of claim 1 wherein the irradiation of the organic carbonate with ultraviolet light is carried out for at least 10 minutes.

* * * * *